US00PP10723P

United States Patent [19]

Butcher

[11] Patent Number: Plant 10,723

[45] Date of Patent: Dec. 15, 1998

[54] CHRYSANTHEMUM PLANT NAMED 'KIAH'

[76] Inventor: Thomas A. Butcher, 800 Field St., Lakewood, Colo. 80215

[21] Appl. No.: 835,502

[22] Filed: Apr. 2, 1997

[51] Int. Cl.[6] ..... A01H 5/00

[52] U.S. Cl. ..... Plt./76

[58] Field of Search ..... Plt./76, 82, 79

*Primary Examiner*—Howard J. Locker

*Attorney, Agent, or Firm*—Christie, Parker & Hale, LLP

[57] ABSTRACT

A new variety of Chrysanthemum plant having a cymose cluster inflorescence form producing reddish bronze flowers of the decorative type in the shape of an irregular circle.

2 Drawing Sheets

BACKGROUND OF THE INVENTION

The present invention is directed to a new and distinct variety of Chrysanthemum botanically classified as *Dendranthema grandiflora*. The varietal denomination of the new chrysanthemum is 'Kiah'.

'Kiah' was discovered as a natural mutation in a controlled cultivated planting of the variety 'Coral Pomona,' U.S. Plant Pat. No. 7,841. The new variety has been asexually reproduced by vegetative cuttings in Ventura County, Calif. and the distinguishing characteristics are retained through successive generations of asexual reproduction.

SUMMARY OF THE INVENTION

'Kiah' is a pot forcing chrysanthemum plant variety producing reddish bronze flowers and capable of being grown commercially in a greenhouse.

Comparison With Parent

'Kiah' differs from the parent 'Coral Pomona' in ray floret color and height, with 'Kiah' somewhat shorter than the parent variety.

BRIEF DESCRIPTION OF ILLUSTRATIONS

The accompanying photographs show typical specimens of the new variety with colors being as nearly true as possible with illustrations of this type.

DESCRIPTION OF THE PLANT

Figure 1:
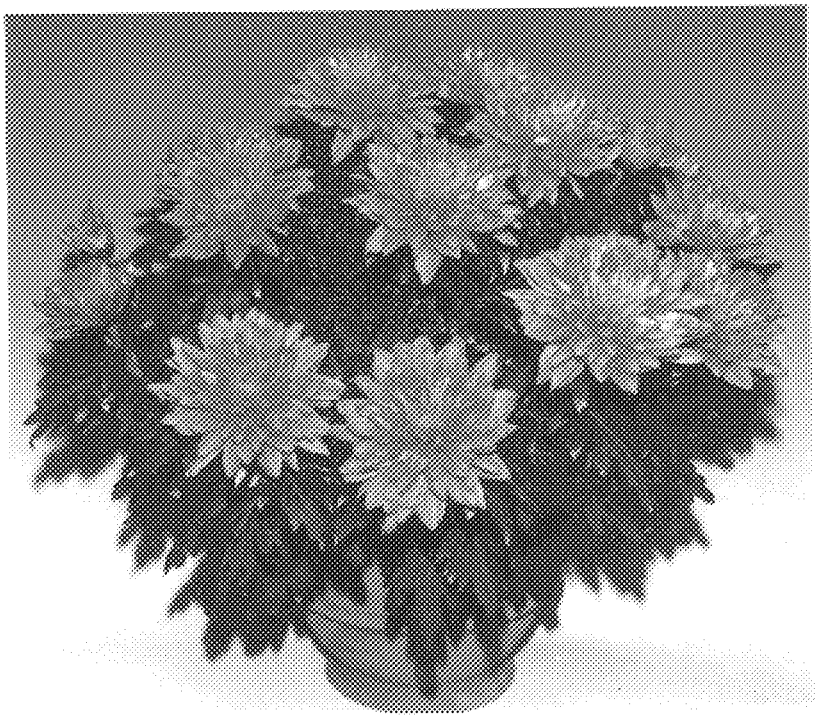
FIG. 1 shows the cultivar when grown as a pinched spray pot mum.
Figure 2:
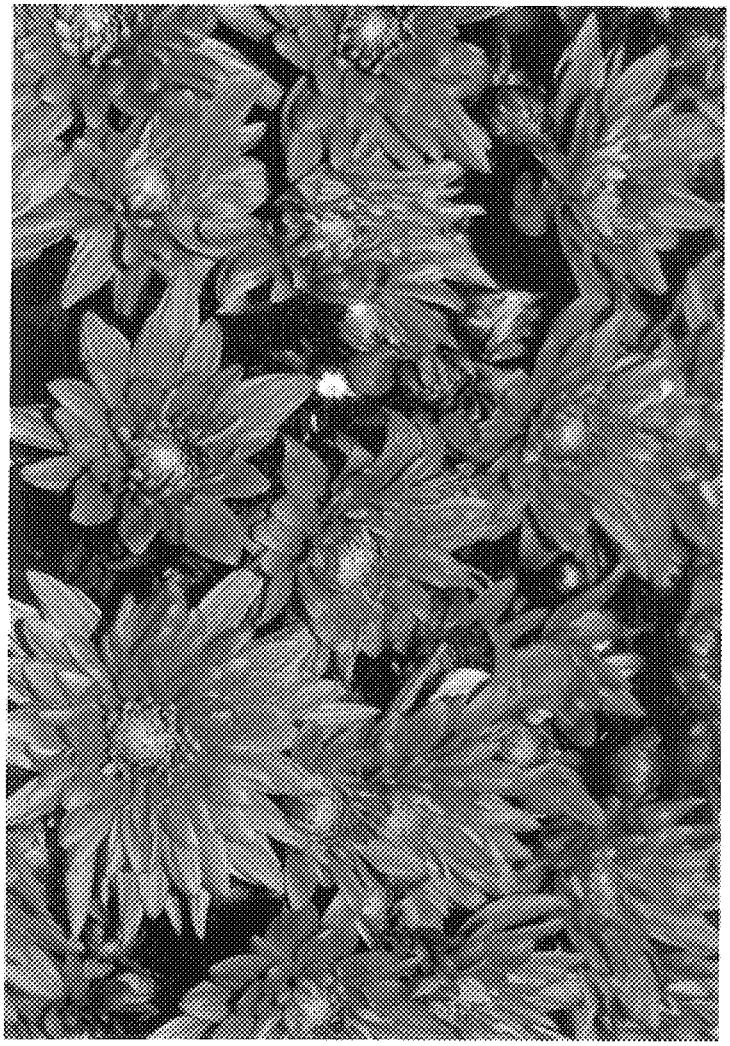
FIG. 2 is a close-up view of typical inflorescences.

The following description of the new variety is of specimens grown in a greenhouse in Ventura County, Calif. in the month of October. 'Kiah' has not been observed under all possible environmental conditions. The phenotype may vary significantly with variations in the environment such as temperature, light intensity, day length and cultural conditions.

Plants of the new variety have been grown successfully under temperature conditions averaging about 65° F. at night and about 75°–85° F. during the day under light conditions of about 5,000–6,000 foot candles. The plants respond well to use of growth retardant, such as one 09 treatment at about 2500 ppm. To produce a commercial product the plants may be pinched once with the center bud removed. It has been observed that the shelf of 'Kiah' is about 20 days with the response time of about 9 weeks. Color values are taken from The Royal Horticultural Society Colour Chart (R.H.S.C.C.).

Plant

Habit: Branching, somewhat spreading. 'Kiah' is used as a potted plant. Shelf life of the potted plant is around 20 days.

Height: About 21 cm.

Branching characteristics: Strong branches both in quality and quantity.

Number of breaks from pinch: About 4.

Typical container size to be grown in: 4", 6", 8", 10".

Length of lateral branches: Average — about 15 cm.

Stem color: Near 144C.

Foliage

Leaf arrangement: Alternate.

Number of leaves per lateral branch: Average — about 9, not very leafy, but appears full.

(1) *Size.*—Length — Average about 7.9 cm. Width — Average about 4.4 cm.

(2) *Shape.*—Ovate.

(3) *Attachment.*—Petioled.

(4) *Apex.*—Obtuse with serration at tip.

(5) *Base.*—Tapered.

| (6) | Color: | Mature | Young |
|---|---|---|---|
| | Top: | Near 137A | Near 137B |
| | Bottom: | Near 138B | Near 138B |

Margin: Lobed with serrations.

Aspect: Whole leaf curled down slightly.

Surface characteristics:

*Top.*—Puberulent.

*Bottom.*—Puberulent.

Venation: Net, with prominent mid-vein. Main veins are prominent on underside of leaf. Main vein coloration is near 144B. Veinlet coloration is near 137B.

Petiole:

(1) *Length.*—About 2.2 cm.

(2) *Color.*—Near 144B.

(3) *Other characteristics.*—Winged, tomentose.

Stipule: Not present.

Flower

Inflorescence form: Cymose cluster.

Flower:

*Form.*—Decorative.

*Shape.*—Flat.

*Color* (*general*).—Red-Bronze with yellow under petals. Blooms: About 4 blooms per branch.

(1) *Diameter.*—About 10 cm.

(2) *Depth.*—About 2.3 cm.

Sepal:

(1) *Number.*—About 40.

(2) *Color.*—Near 147A.

(3) *General appearance.*—Very membranous edges, green fleshy part is only a straight, narrow strip, margins entire and membranous shape is concave-convex.

Peduncle:

(1) *Length.*—Average about 5.5 cm.

(2) *Habit.*—Upright in middle, curved on outer branches.

(3) *Surface.*—Tomentose.

(4) *Color.*—Near 144A.

(5) *Strength.*—Sturdy.

Bud:

(1) *Shape.*—Half sphere, flat top.

(2) *Diameter.*—Avg. about 1 cm.

(3) *Color.*—Near 162B.

(4) *Height.*—About 0.6 cm.

Ray florets:

(1) *Number per flower.*—About 230.

(2) *Fused.*—No.

(3) *Texture.*—Dull matte.

(4) *Shape.*—Elliptic.

(5) *Apex.*—Older flowers develop 3 very small lobes, younger flowers have no lobes.

(6) *Base.*—Tapered.

(7) *Margin.*—Entire.

(8) *Aspect.*—Revolute.

(9) *Length.*—Avg. About 4.6 cm.

(10) *Width.*—Avg. About 1.4 cm.

*Color — top side.*—Immature: Near 179A with faint yellow streaks. Mature: Near 181B with faint yellow streaks. Fading: Near 184A, faint yellow streaks.

*Color — under side.*—Immature: Near 162B with streaks of near 180A. Mature: Near 181C with yellow streaks. Fading: Near 181A with yellow stripes.

Disc florets:

(1) *Number per flower.*—About 30.

(2) *Texture.*—Shiny.

(3) *Shape.*—Cylindric.

(4) *Margin.*—Entire.

(5) *Length.*—About 0.5 cm.

(6) *Width.*—About 0.12 cm.

(7) *Fragrance.*—Light, musky.

*Color.*—Immature: Near 17C with light green tip. Mature: Near 17C with light green tip, white base. Fading: Near 15B.

Description of flower as it ages: Center becomes almost completely yellow and develops an eye. Yellow streaks become more prominent, but reddish coloration does not fade.

Reproductive Organs

Ray florets:

*Pistillate.*—(1) Pistil number: 1 per flower. (2) Receptacle shape: Half sphere. (3) Stigma shape: Forked, curling out almost perpendicular. (4) Stigma color: Near 17B. (5) Style length: About 0.4 cm. (6) Style color: Near 154C.

Disc florets:

*Pistillate.*—(1) Pistil number: 1 per flower. (2) Stigma shape: Linear. (3) Style length: About 0.2 cm.

*Staminate.*—(1) Stamen number: About 6. (2) Anther length: About 0.2 cm. (3) Anther shape: Linear. (4) Pollen color: Near 23A. (5) Pollen quantity: Abundant.

What is claimed is:

1. A new and distinct variety of Chrysanthemum plant substantially as herein shown and described.

* * * * *

UNITED STATES PATENT AND TRADEMARK OFFICE

CERTIFICATE OF CORRECTION

PATENT NO. : Plant 10,723
DATED : December 15, 1998
INVENTOR(S) : Thomas A. Butcher It is certified that error appears in the above-identified patent and that said Letters Patent is hereby corrected as shown below:

Column 1, line 48, change "09" to -- B9 --.

Column 3, lines 1-4, for proper form lines 1-4 should read as follows:

-- *Color (general).*—Red-Bronze with yellow under petals.
Blooms: About 4 blooms per branch.
(1) *Diameter.*—About 10 cm.
(2) *Depth.*—About 2.3 cm. --.

Column 4, lines 24, 25, change "Recaptacle" to -- Receptacle --.

Signed and Sealed this

Twenty-eighth Day of March, 2000

*Attest:*

Q. TODD DICKINSON

*Attesting Officer*

*Commissioner of Patents and Trademarks*